(12) United States Patent
Yokozeki et al.

(10) Patent No.: US 6,197,552 B1
(45) Date of Patent: *Mar. 6, 2001

(54) PROCESS FOR PREPARING 2,6-DIAMINOPURINE-2'-DEOXYRIBOSIDE AND 2'-DEOXYGUANOSINE

(75) Inventors: Kenzo Yokozeki; Takashi Tsuji; Kunisuke Izawa, all of Kawasaki (JP)

(73) Assignee: Ajinomoto Co., Inc., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/192,286

(22) Filed: Nov. 15, 1998

(30) Foreign Application Priority Data

Nov. 14, 1997 (JP) ................................... 9-313207

(51) Int. Cl.$^7$ .................................................. C12P 19/40
(52) U.S. Cl. ................................ 435/88; 435/84; 435/85; 435/87
(58) Field of Search ............................... 435/88, 87, 85, 435/84

(56) References Cited

U.S. PATENT DOCUMENTS

| | | | |
|---|---|---|---|
| 3,269,917 | * | 8/1966 | Imada et al. ............................ 435/88 |
| 4,347,315 | | 8/1982 | Krenitsky et al. . |
| 4,381,344 | | 4/1983 | Rideout et al. . |
| 4,835,104 | | 5/1989 | Yokozeki et al. . |
| 4,970,148 | | 11/1990 | Yokozeki et al. . |
| 5,384,251 | * | 1/1995 | Yamauchi et al. ..................... 435/87 |
| 5,486,603 | * | 1/1996 | Buhr .................................... 536/24.3 |

FOREIGN PATENT DOCUMENTS

| | | |
|---|---|---|
| 0 002 192 | 6/1979 | (EP) . |
| 1 063 951 | 4/1967 | (GB) . |

OTHER PUBLICATIONS

Utagawa et al, Agric. Biol. Chem. 49(9):2711–2717, 1985.*

* cited by examiner

*Primary Examiner*—Francisco Prats
(74) *Attorney, Agent, or Firm*—Oblon, Spivak, McClelland, Maier & Neustadt, P.C.

(57) ABSTRACT

A process for preparing 2,6-diaminopurine-2'-deoxyriboside and 2'-deoxyguanosine. These compounds may be used as materials for pharmaceuticals, such as antiviral agents and the like, and particularly as starting materials for antisense oligonucleotides.

5 Claims, No Drawings

PROCESS FOR PREPARING 2,6-DIAMINOPURINE-2'-DEOXYRIBOSIDE AND 2'-DEOXYGUANOSINE

BACKGROUND OF THE INVENTION

1. Field of the Invention

The present invention relates to a process for preparing 2,6-diaminopurine-2'-deoxyriboside and 2'-deoxyguanosine. These compounds are used as materials for pharmaceuticals such as antiviral agents and the like, and particularly as starting materials for antisense drugs, which are highly desired pharmaceuticals.

2. Discussion of the Related Art

Since the yield in chemical synthesis for producing 2'-deoxyguanosine is very low, the industrial production thereof has mainly been performed via extraction of a hydrolysate of DNA (deoxyribonucleic acid). In the conventional extraction process, however, the hydrolysate of DNA contains 2'-deoxyadenosine, 2'-deoxycytidine and thymidine, in addition to the desired 2'-deoxyguanosine. Therefore, from the viewpoint of this troublesome and costly extraction step for collecting 2'-deoxyguanosine alone, the development of a more effective process has been in great demand.

SUMMARY OF THE INVENTION

Accordingly, an object of the present invention is to provide a process for producing 2,6-diaminopurine-2'-deoxyriboside and 2'-deoxyguanosine in high yield and with good efficiency.

As the result of an extensive research for establishing a process for preparing 2'-deoxyguanosine with good efficiency, the present inventors have found that:

(1) 2,6-diaminopurine-2'-deoxyriboside can be produced with good efficiency by contacting 2'-deoxyribose-1-phosphoric acid or a salt thereof and 2,6-diaminopurine or a salt thereof with a microorganism;

(2) 2,6-diaminopurine-2'-deoxyriboside can be produced with good efficiency by contacting 2'-deoxyuridine or thymidine and 2,6-diaminopurine or a salt thereof with a microorganism, in the presence of an inorganic phosphoric acid or a salt thereof, and (3) 2'-deoxyguanosine can be produced in a high yield by putting 2,6-diaminopurine-2'-deoxyriboside, used as a substrate, produced and provided steadily and at low costs by processes (1) and (2) as described above, under the action of adenosine deaminase; and have thus completed the present invention.

Accordingly, the present invention relates to:

(1) a process for preparing 2,6-diaminopurine-2'-deoxyriboside which comprises contacting 2'-deoxyribose-1-phosphoric acid or a salt thereof and 2,6-diaminopurine with a culture of a microorganism having an ability of producing 2,6-diaminopurine-2'-deoxyriboside from 2'-deoxyribose-1-phosphoric acid or a salt thereof and 2,6-diaminopurine, and preferably belonging to a genus selected from the group consisting of Achromobacter, Agrobacterium, Acinetobacter, Alcaligenes, Arthrobacter, Aeromonas, Escherichia, Enterobacter, Erwinia, Xanthomonas, Klebsiella, Kurthia, Kluyvera, Corynebacterium, Sartina, Salmonella, Citrobacter, Pseudomonas, Streptomyces, Sporosarcina, Staphyrococcus, Serratia, Cellulomonas, Nocardia, Bacillus, Hafnia, Vibrio, Flavobacterium, Planococcus, Brevibacterium, Protaminobacter, Proteus, Haemophilus, Micrococcus, Mycoplana, Mycobacterium, Rhizobium and Rhodococcus, or of cells of the microorganism separated from said culture, or of a treatment product of said cells of the microorganism, and collecting the produced 2,6-diaminopurine-2'-deoxyriboside;

(2) a process for preparing 2,6-diaminopurine-2'-deoxyriboside which comprises contacting 2'-deoxyuridine or thymidine and 2,6-diaminopurine with a culture of a microorganism having an ability of producing 2,6-diaminopurine-2'-deoxyriboside from 2'-deoxyuridine or thymidine and 2,6-diaminopurine in the presence of an inorganic phosphoric acid or a salt thereof, and preferably belonging to a genus selected from the group consisting of Achromobacter, Agrobacterium, Acinetobacter, Alcaligenes, Arthrobacter, Aeromonas, Escherichia, Enterobacter, Erwinia, Xanthomonas, Klebsiella, Kurthia, Kluyvera, Corynebacterium, Sartina, Salmonella, Citrobacter, Pseudomonas, Streptomyces, Sporosarcina, Staphyrococcus, Serratia, Cellulomonas, Nocardia, Bacillus, Hafnia, Vibrio, Flavobacterium, Planococcus, Brevibacterium, Protaminobacter, Proteus, Haemophilus, Micrococcus, Mycoplana, Mycobacterium, Rhizobium or Rhodococcus, or of cells of the microorganism separated from said culture, or of a treatment product of said cells of the microorganism, in the presence of an inorganic phosphoric acid or a salt thereof, and collecting the produced 2,6-diaminopurine-2'-deoxyriboside; and (3) a process for preparing 2'-deoxyguanosine which comprises preparing 2,6-diaminopurine-2'-deoxyriboside according to process (1) or (2) above, and then contacting the produced 2,6-diaminopurine-2'-deoxyriboside with an adenosine deaminase or a material containing said enzyme in an aqueous medium to produce and accumulate 2'-deoxyguanosine.

A more complete appreciation of the invention and many of the attendant advantages thereof will be readily obtained as the same becomes better understood by reference to the following detailed description.

DETAILED DESCRIPTION OF THE INVENTION

A wide variety of microorganisms may be used for the production of 2,6-diaminopurine-2'-deoxyriboside according to the present invention, insofar as they have the ability of producing 2,6-diaminopurine-2'-deoxyriboside from 2'-deoxyribose-1-phosphoric acid or a salt thereof and 2,6-diaminopurine or an ability of producing 2,6-diaminopurine-2'-deoxyriboside from 2'-deoxyuridine or thymidine and 2,6-diaminopurine in the presence of an inorganic phosphoric acid or a salt thereof. Microorganisms, for example, belonging to the genus Achromobacter, Agrobacterium, Acinetobacter, Alcaligenes, Arthrobacter, Aeromonas, Escherichia, Enterobacter, Erwinia, Xanthomonas, Klebsiella, Kurthia, Kluyvera, Corynebacterium, Sartina, Salmonella, Citrobacter, Pseudomonas, Streptomyces, Sporosarcina, Staphyrococcus, Serratia, Cellulomonas, Nocardia, Bacterium, Bacillus, Hafnia, Vibrio, Flavobacterium, Planococcus, Brevibacterium, Protaminobacter, Proteus, Haemophilus, Micrococcus, Mycoplana, Microbacterium, Rhizobium or Rhodococcus have such an ability. Specifically, examples may include the microorganisms listed below:

*Achromobacter viscosus* ATCC 12448,
*Agrobacterium tumefaciens* ATCC 4720,

Acinetobacter johnsonii ATCC 9036,
Alcaligenes faecalis subsp. faecalis ATCC 8750,
Arthrobacter oxydans ATCC 14358,
Aeromonas salmonicida subsp. salmonicida ATCC 14174,
Escherichia coli ATCC 10798,
Enterobacter cloacae ATCC 7256,
Erwinia herbicola ATCC 1453,
Xanthomonas citri AJ 2785 (FERM BP-6560),
Klebsiella pneumoniae IFO 3321,
Kurthia zopfii ATCC 6900,
Kluyvera citrophila AJ 2626 (FERM BP-6564),
Corynebacterium acetoacidophilum ATCC 21407,
Sartina lutea AJ 1218 (FERM BP-6562),
Salmonella typhimurium AJ 2636 (FERM BP-6561),
Citrobacter freundi ATCC 8090,
Pseudomonas diminuta ATCC 11568,
Streptomyces tanashiens ATCC 15238,
Sporosarcina ureae IFO 12698,
Staphyrococcus epidermidis ATCC 155,
Serratia marcescens ATCC 14226,
Cellulomonas flavigera ATCC 486,
Nocardia asteroides ATCC 19247,
Bacillus subtilis ATCC 6633,
Hafnia alvei ATCC 9760,
Vibrio metschnikovii ATCC 7708,
Flavobacterium breve ATCC 14234,
Planococcus eucinatus AJ 1656 (FERM BP-6493),
Brevibacterium pusillum ATCC 19096,
Protaminobacter alboflavus ATCC 8458,
Proteus rettegeri AJ 2770 (FERM BP-941),
Haemophilus influenzae ATCC 9134,
Micrococcus luteus ATCC 4698,
Mycoplana dimorpha ATCC 4279,
Mycobacterium lacticum ATCC 8180,
Rhizobium melilotti AJ 2823 (FERM BP-6565) and
Rhodococcus rhodochraus ATCC 19149.

Among the strains described above, *Xanthomonas citri* AJ 2785 is a strain having an accession number of FERM BP-6560, originally deposited at the Fermentation Research Institute, Agency of industrial Science and Technology, Ministry of International Trade and Industry (now the National Institute of Bioscience and Human-Technology, Agency of industrial Science and Technology, Ministry of International Trade and Industry) with an accession number of FERM P-3396 on Jan. 27, 1976, and converted to an international deposit under the Budapest Treaty on Nov. 2, 1998; *Kluyvera citrophila* AJ 2626 is a strain having an accession number of FERM BP-6564, originally deposited at the same depositary authority with an accession number of FERM P-8193 on Apr. 23, 1985, and converted to an international deposit under the Budapest Treaty on Nov. 2, 1998; *Sartina lutea* AJ 1218 is a strain having an accession number of FERM BP-6562, originally deposited at the same depositary authority with an accession number of FERM P-7400 on Jan. 20, 1984, and converted to an international deposit under the Budapest Treaty on Nov. 2, 1998; *Salmonella typhimurium* AJ 2636 is a strain having an accession number of FERM BP-6561, originally deposited at the same depositary authority with an accession number of FERM P-3753 on Oct. 6, 1976, and converted to an international deposit under the Budapest Treaty on Nov. 2, 1998; *Planococcus eucinatus* AJ 1656 is a strain having an accession number of FERM BP-6493, originally deposited at the same depositary authority with an accession number of FERM P-9133 on Jan. 19, 1987, and converted to an international deposit under the Budapest Treaty on Sep. 9, 1998; *Proteus rettegeri* AJ 2770 is a strain having an accession number of FERM BP-941, originally deposited at the same depositary authority with an accession number of FERM P-8196 on Apr. 25, 1985, and converted to an international deposit under the Budapest Treaty on Nov. 28, 1985; and *Rhizobium melilotti* AJ 2823 is a strain having an accession number of FERM BP-6565 originally deposited at the same depositary authority with an accession number of FERM P-8197 on Apr. 25, 1985, and converted to an international deposit under the Budapest Treaty on Nov. 2, 1998.

The process for producing 2,6-diaminopurine-2'-deoxyriboside using these microorganisms may either be one using a culture method in which a substrate is added during the culturing of a microorganism or one using a resting cell method in which a substrate is put under the action of cultured cells or a treatment product thereof.

When the culture method is used, a routine medium can be used containing a carbon source, a nitrogen source, a phosphorus source, a sulfur source, inorganic ions and so on, together with vitamins and an organic nitrogen source, if necessary.

As the carbon source, carbohydrates may be used, such as glucose or the like. Alcohols such as glycerol or the like, and organic acids such as acetic acid or the like, may also be used as the carbon source. As the nitrogen source are used gaseous ammonia, aqueous ammonia, ammonium salts, nitric acid and salts thereof and the like. As the phosphorus source are used inorganic phosphoric acid and salts thereof such as monopotassium phosphate and the like. As the sulfur source are used magnesium sulfate and the like. As the inorganic ions are used magnesium ion, potassium ion, iron ion, manganese ion and so on, appropriately. As the organic nutrient source are appropriately used vitamins, amino acids and the like as well as yeast extract, peptone, meat extract, corn steep liquor, casein hydrolysate and the like containing them. There is also no limitation in culturing conditions, and the culture may be conducted, for example, under an aerobic condition, within ranges of pH of 5 to 8 and of temperature of 25 to 40° C. with appropriate control of pH and a reaction time of about 12 to 72 hours.

Specifically, a microorganism is cultured with appropriate addition of (1) 2'-deoxyribose-1-phosphoric acid and 2,6-diaminopurine to the basal medium described above when 2,6-diaminopurine-2'-deoxyriboside is produced from 2'-deoxyribose-1-phosphoric acid or (2) 2'-deoxyuridine or thymidine and 2,6-diaminopurine to the basal medium described above when 2,6-diaminopurine-2'-deoxyriboside is produced from 2'-deoxyuridine or thymidine. The addition of the substrate described above may either be carried out at the initial stage of the culture or in the middle of the culture.

For the case in which the resting cell method is used, a culture solution per se obtained by the above methods or washed cells as well as a treatment product of the cells can be used as the enzyme source. As the treatment product of the cells can be used anyone of acetone-dried cells, triturated cells, a treatment product of cells with ultrasonic oscillator or Dynomill or French press, cells contacted with a surfactant, toluene or the like, cells treated with an enzyme such as lysozyme, protease or the like, a protein fraction separated by treating a cell extract with dialysis or the like, a purified enzyme having an enzymatic activity for this reaction, as well as an immobilized, product of the cells or treatment product.

Specifically, the reaction is carried out with appropriate addition of the cells of microorganism or the treatment product to an aqueous solution containing (1) 2-deoxyribose-1-phosphoric acid and 2,6-diaminopurine when 2,6-diaminopurine-2'-deoxyriboside is produced from 2-deoxyribose-1-phosphoric acid or (2) 2'-deoxyuridine or thymidine, 2,6-diaminopurine and an inorganic phosphoric acid or a salt thereof when 2,6-diaminopurine-2'-deoxyriboside is produced from 2'-deoxyuridine or thymidine.

The reaction is usually carried out at a temperature of 20 to 80° C., preferably of 40 to 70° C., and pH of 3 to 11, preferably of 4 to 10 with a favorable result. The reaction may be conducted either by the standing method or by stirring method. While the exact reaction period depends on the activity of the enzyme used and the concentration of the substrate, the reaction may generally be conducted for 10 minutes–10 days.

It is possible to prepare 2'-deoxyguanosine by putting 2,6-diaminopurine-2'-deoxyriboside obtained above under the action of an adenosine deaminase or a material containing said enzyme in an aqueous medium. The action of the adenosine deaminase may either be effected on 2,6-diaminopurine-2'-deoxyriboside in the reaction solution described above without separation or on a product separated from the mixture after reaction. The method for collection or separation includes a method using a synthetic adsorption resin and other routine collecting or separating methods.

The adenosine deaminase is an enzyme capable of converting adenosine to inosine. The present inventors have found that the adenosine deaminase is also capable of converting 2,6-diaminopurine-2'-deoxyriboside to 2'-deoxyguanosine. Therefore, the adenosine deaminase used in the production of 2'-deoxyguanosine from 2,6-diaminopurine-2'-deoxyriboside by the action of the adenosine deaminase according to the present invention may be anyone irrespective of origin insofar as it is capable of converting 2,6-diaminopurine-2'-deoxyriboside to 2'-deoxyguanosine. Specific usable examples include those of animal origin such as one originating from bovine intestine, spleen or the like and those of microorganism origin such as one described in Handbook of Enzyme (page 605 8th Ed., published by Asakura-shoten, Apr. 20, 1993, incorporated herein by reference).

In addition, it is also possible to use an adenosine deaminase originating from a microorganism belonging to the genus Acinetobacter, Aeromonas, Alcaligenes, Arthrobacter, Bacillus, Brevibacterium, Cellulomonas, Citrobacter, Corynebacterium, Escherichia, Enterobacter, Erwinia, Flavobacterium, Hafnia, Klebsiella, Kluyvera, Microbacterium, Micrococcus, Mycoplana, Nocardia, Planococcus, Protaminobacter, Proteus, Pseudomonas, Rhizobium, Rhodococcus, Salmonella, Serratia, Staphyrococcus, Streptomyces, Vibrio or Xanthomonas and capable of converting 2',3'-dideoxyadenosine to 2',3'-dideoxyinosine, as described in Unexamined Japanese Patent Publication No. Hei 02-291291. Specifically, adenosine deaminases originating from microorganisms listed below can be used:
*Acinetobacter lwoffii* ATCC 9036,
*Aeromonas salmonicida* ATCC 14174,
*Alcaligenes faecalis* AJ 2541 (FERM BP-940),
*Arthrobacter citreus* ATCC 11624,
*Bacillus firmus* ATCC 8247,
*Brevibacterium pusillum* ATCC 19096,
*Cellulomonas flavigena* ATCC 491,
*Citrobacter freundii* ATCC 8090,
*Corynebacterium aquaticum* ATCC 14665,
*Escherichia coli* AJ 2634 (FERM BP-6563),
*Enterobacter cloacae* ATCC 13047,
*Erwinia carotovora* AJ 2753 (FERM BP-6559),
*Flavobacterium aquatile* ATCC 8375,
*Hafnia alvei* ATCC 9760,
*Klebsiella pneumoniae* ATCC 8308,
*Kluyvera citrophila* AJ 2626 (FERM BP-6564),
*Microbacterium imperiable* ATCC 8365,
*Micrococcus luteus* ATCC 400,
*Mycoplana dimorpha* ATCC 4279,
*Nocardia restricts* ATCC 14887,
*Planococcus citreus* ATCC 15234,
*Protaminobacter alboflavus* ATCC 8458,
*Proteus rettgeri* AJ 2770 (FERM BP-941),
*Pseudomonas oleovorans* ATCC 8062,
*Rhizobium meliloti* AJ 2823 (FERM BP-6565),
*Rhodococcus rhodochrous* ATCC 12974,
*Salmonella typhimurium* AJ 2635 (FERM BP-6566),
*Arthrobacter ureafaciens* AJ 1210 (FERM BP-2472),
*Serratia grimesii* ATCC 14460,
*Staphyrococcus epidermidis* ATCC 155,
*Streptomyces flavovirens* IFO 3197,
*Vibrio metschnikovii* ATCC 7708 and
*Xanthomonas citri* AJ 2785 (FERM BP-6560), Among the strains described above, *Xanthomonas citri* AJ 2785 is a strain having an accession number of FERM BP-6560, originally deposited at the Fermentation Research Institute, Agency of industrial Science and Technology, Ministry of International Trade and Industry (now the National Institute of Bioscience and Human-Technology, Agency of industrial Science and Technology, Ministry of International Trade and Industry) with an accession number of FERM P-3396 on Jan. 27, 1976, and converted to an international deposit under the Budapest Treaty on Nov. 2, 1998; *Kluyvera citrophila* AJ 2626 is a strain having an accession number of FERM BP-6564, originally deposited at the same depositary authority with an accession number of FERM P-8193 on Apr. 23, 1985, and converted to an international deposit under the Budapest Treaty on Nov. 2, 1998; *Arthrobacter ureafaciens* AJ 1210 is a strain having an accession number of FERM BP-2472, originally deposited at the same depositary authority with the original identification of *Sarcina albida* AJ 1210 and an accession number of FERM P-7048 on Apr. 25, 1983, and converted to an international deposit under the Budapest Treaty on Jun. 14, 1989; *Salmonella typhimurium* AJ 2635 is a strain having an accession number of FERM BP-6566, originally deposited at the same depositary authority with an accession number of FEPM P-9470 on Jul. 11, 1987, and converted to an international deposit under the Budapest Treaty on Nov. 2, 1998; *Escherichia coli* AJ 2634 is a strain having an accession number of FERM BP-6563, originally deposited at the same depositary authority with an accession number of FERM P-7404 on Jan. 20, 1984, and converted to an international deposit under the Budapest Treaty on Nov. 2, 1998; *Proteus rettegeri* AJ 2770 is a strain having an accession number of FERM BP-941, originally deposited at the same depositary authority with an accession number of FEPM P-8196 on Apr. 25, 1985, and converted to an international deposit under the Budapest Treaty on Nov. 28, 1985; *Rhizobium melilotti* AJ 2823 is a strain having an accession number of FERM BP-6565, originally deposited at the same depositary authority with an accession number of FERM P-8197 on Apr. 25, 1985, and converted to an international deposit under the Budapest Treaty on Nov. 2, 1998; *Alcaligenes faecalis* AJ 2541 is a strain having an accession number of FERM BP-940, originally deposited at the same depositary authority with an accession number of FERM P-8030 on Dec. 24, 1984, and converted to an international deposit under the Budapest Treaty on Nov. 28, 1985, *Erwinia carotovora* AJ 2753 is a strain having an accession number of FERM BP-6559, originally deposited at the same depositary authority with an accession number of FERM P-2766 on Oct. 29, 1974, and converted to an international deposit under the Budapest Treaty on Nov. 2, 1998.

On the other hand, as the material containing said enzyme (adenosine deaminase), a culture solution and cultured cells of the microorganism described above can be used. In addition, also usable are treatment products of cells including acetone-treated cells, triturated cells, cells treated with a surfactant, toluene or the like, cells treated with an enzyme such as lysozyme or the like, a protein fraction separated by treating a cell extract with salting out, column chromatography or the like, a purified product of protein fraction having an adenosine deaminase activity for this reaction, as well as an immobilized product of the cells or cell-treatment product. As the material containing said enzyme derived from animals or plants, a triturated product of a part containing said enzyme and treatment products or immobilized products similar to those of microorganism-derived enzyme can be used.

The method for acting the adenosine deaminase on 2,6-diaminopurine-2'-deoxyriboside may be effected by adding the adenosine deaminase to a solution containing 2,6-diaminopurine-2'-deoxyriboside to cause the reaction. The reaction in which the adenosine deaminase is reacted on 2,6-diaminopurine-2'-deoxyriboside is usually carried out at a temperature of 5 to 50° C., desirably of 10 to 40° C., and pH of 4 to 10, desirably of 5 to 9 with a favorable result. The reaction may be conducted either by the standing method or by stirring method. During the reaction, ammonia is produced by the action of said enzyme and increase pH of the reaction solution. A favorable result can be obtained when pH is adjusted according to the optimum pH of the enzyme. While the reaction period depends on the activity of the enzyme used and the concentration of the substrate, the reaction may be kept for 10 minutes to 5 days.

Besides, the quantitative analysis of 2,6-diaminopurine-2'-deoxyriboside and 2'-deoxyguanosine may be carried out by a method using the high performance liquid chromatography.

The yield of the collected 2,6-diaminopurine-2'-deoxyriboside is preferably at least 10%, more preferably at least 50%, even more preferably at least 75%, and, most preferably, at least 90%. Yields as high as at least 99% are especially preferred.

The yield of the collected 2'-deoxyguanosine is preferably at least 10%, more preferably at least 50%, even more preferably at least 75%, and, most preferably, at least 90%. Yields as high as at least 99% are especially preferred.

The 2,6-diaminopurine-2'-deoxyriboside and 2'-deoxyguanosine may be used to prepare a wide variety of pharmaceuticals. An especially preferred class of pharmaceuticals is oligonucleotides, or analogs thereof. The 2,6-diaminopurine-2'-deoxyriboside and/or 2'-deoxyguanosine may be incorporated into an oligonucleotide during the synthesis thereof. The synthesis of oligonucleotides, e.g., antisense oligonucleotides, is well-known. See, for example, *Nucleic Acids in Chemistry and Biology*, G. M. Blackburn and M. J. Gait, Eds., IRL Press 1990, especially pp. 73–133, the entire contents of which is incorporated herein by reference. During synthesis, the 2,6-diaminopurine-2'-deoxyriboside and 2'-deoxyguanosine may be protected with suitable protecting groups as is well-known in the art. The length of the oligonucleotides may vary widely. The oligonucleotides may have a length of, for example, 5 to 100 nucleotides.

Having generally described this invention, a further understanding can be obtained by reference to certain specific examples which are provided herein for purposes of illustration only and are not intended to be limiting unless otherwise specified.

EXAMPLES

Example 1

Into a Sakaguchi flask (500 ml) was placed 50 ml of a nutrient medium (pH 7.0) containing 5 g/l yeast extract, 10 g/l meat extract, 10 g/l peptone and 5 g/l NaCl and sterilized at 120° C. for 20 minutes. One platinum loop of each of the microorganisms listed in Table 1, cultured on the bouillon agar slant at 30° C. for 16 hours, was inoculated to this and cultured with shaking at 30° C. for 18 hours. Cells were separated from the obtained culture by centrifugation, then washed with 50 mM Tris-HCl buffer (pH 7.2) and centrifuged again to prepare washed cells.

The washed cells described above were added to 10 ml of 50 mM Tris-HCl buffer (pH 7.2) containing 100 mM 2'-deoxyribose-1-phosphoric acid and 100 mM 2,6-diaminopurine hemisulfate to a washed cell-concentration of 50 g/ and reacted at 60° C. for 2 hours. The concentration of 2,6-diaminopurine-2'-deoxyriboside produced in the reaction solution was measured by high performance liquid chromatography. The results are shown in Table 1.

TABLE 1

| Microorganism | Yield (g/l) |
| --- | --- |
| *Achromobacter viscosus* ATCC 12448 | 2.7 |
| *Agrobacterium tumefaciens* ATCC 4720 | 7.9 |
| *Acinetobacter johnsonii* ATCC 9036 | 7.8 |
| *Alcaligenes faecalis* subsp. faecalis ATCC 8750 | 5.0 |
| *Arthrobacter oxydans* ATCC 14358 | 6.9 |
| *Aeromonas salmonicida* subsp. salmonicida ATCC 14174 | 3.3 |
| *Escherichia coli* ATCC 10798 | 1.6 |
| *Enterobacter cloacae* ATCC 7256 | 6.2 |
| *Erwina herbicola* ATCC 1453 | 3.7 |
| *Xanthomonas citri* AJ 2785 (FERN BP-6560) | 1.6 |
| *Klebsiella pneumoniae* IFO 3321 | 17.2 |
| *Kurthia zopfii* ATCC 6900 | 2.8 |
| *Kluyvera citrophila* AJ 2626 (FERM BP-6564) | 5.6 |
| *Cornyebacterium acetoacidophilum* ATCC 21407 | 3.1 |
| *Sartina lutea* AJ 1218 (FERM BP-6562) | 6.9 |
| *Salmonella typhimurium* AJ 2636 (FERM BP-6561) | 6.8 |
| *Citrobacter freundi* ATCC 8090 | 3.9 |
| *Pseudomonas diminuta* ATCC 11568 | 1.5 |
| *Streptomyces Tanashiens* ATCC 15238 | 1.5 |
| *Sporosarcina ureae* IFO 12698 | 2.7 |
| *Staphyrococcus epidermidis* ATCC 155 | 2.9 |
| *Serratia marcescens* ATCC 14226 | 5.4 |
| *Cellulomonas flavigera* ATCC 486 | 4.7 |
| *Nocardia asteroides* ATCC 19247 | 4.6 |
| *Bacillus subtilis* ATCC 6633 | 3.7 |
| *Hafria alvei* ATCC 9760 | 3.3 |
| *Vibrio metschnikovii* ATCC 7708 | 6.7 |
| *Flavobacterium breve* ATCC 14234 | 3.9 |
| *Planococcus eucinatus* AJ 1656 (FERM BP-6493) | 3.6 |
| *Brevibacterium pusillum* ATCC 19096 | 3.5 |
| *Protaminobacter alboflavus* ATCC 8458 | 2.6 |
| *Proteus rettegeri* AJ 2770 (FERM BP-941) | 3.1 |
| *Haemophilus influenzae* ATCC 9134 | 2.9 |
| *Micrococcus luteus* ATCC 4698 | 5.7 |
| *Mycoplana dimorpha* ATCC 4279 | 7.2 |
| *Microbacterium lacticum* ATCC 8180 | 3.6 |
| *Rhizobium melilotti* AJ 2823 (FERM BP-6565) | 2.1 |
| *Rhodococcus rhodochraus* ATCC 19149 | 6.0 |

Example 2

Into a Sakaguchi flask (500 ml) was placed 50 ml of a nutrient medium (pH 7.0) containing 5 g/l yeast extract, 10 g/l meat extract, 10 g/l peptone and 5 g/l NaCl and sterilized at 120° C. for 20 minutes. One platinum loop of each of the microorganisms listed in Table 2, cultured on the bouillon agar slant at 30° C. for 16 hours, was inoculated to this and cultured with shaking at 30° C. for 18 hours. Cells were separated from the obtained culture by centrifugation, then washed with 50 mM phosphate buffer (pH 7.0) and centrifuged again to prepare washed cells.

The washed cells described above were added to 10 ml of 50 nM phosphate buffer (pH 7.0) containing 100 mM 2'-deoxyuridine and 100 mM 2,6-diaminopurine hemisulfate to a washed cell-concentration of 50 g/l and reacted at 60° C. for 2 hours.

The concentration of 2,6-diaminopurine-2'-deoxyriboside produced in the reaction solution was measured by high performance liquid chromatography. The results are shown in Table 2.

TABLE 2

| Microorganism | Yield (g/l) |
|---|---|
| Achromobacter viscosus ATCC 12448 | 2.1 |
| Agrobacterium tumefaciens ATCC 4720 | 7.0 |
| Acinetobacter johnsonii ATCC 9036 | 7.4 |
| Alcaligenes faecalis subsp. faecalis ATCC 8750 | 5.3 |
| Arthrobacter oxydans ATCC 14358 | 6.2 |
| Aeromonas salmonicida subsp. salmonicida ATCC 14174 | 3.1 |
| Escherichia coli ATCC 10798 | 1.8 |
| Enterobacter cloacae ATCC 7256 | 6.9 |
| Erwina herbicola ATCC 1453 | 3.8 |
| Xanthomonas citri AJ 2785 (FERN BP-6560) | 1.6 |
| Klebsiella pneumoniae IFO 3321 | 16.7 |
| Kurthia zopfii ATCC 6900 | 2.3 |
| Kluyvera citrophila AJ 2626 (FERM BP-6564) | 5.9 |
| Corryebacterium acetoacidophilum ATCC 21407 | 3.8 |
| Sartina lutea AJ 1218 (FERM BP-6562) | 6.7 |
| Salmonella typhimurium AJ 2636 (FERM BP-6561) | 7.1 |
| Citrobacter freundi ATCC 8090 | 3.6 |
| Pseudomonas diminuta ATCC 11568 | 1.2 |
| Streptomyces Tanashiens ATCC 15238 | 1.8 |
| Sporosarcina ureae IFO 12698 | 2.8 |
| Staphyrococcus epidermidis ATCC 155 | 2.7 |
| Serratia marcescens ATCC 14226 | 5.1 |
| Cellulomonas flavigera ATCC 486 | 4.0 |
| Nocardia asteroides ATCC 19247 | 4.6 |
| Bacillus subtilis ATCC 6633 | 3.8 |
| Hafria alvei ATCC 9760 | 3.4 |
| Vibrio metschnikovii ATCC 7708 | 6.7 |
| Flavobacterium breve ATCC 14234 | 3.3 |
| Planococcus eucinatus AJ 1656 (FERM BP-6493) | 3.9 |
| Brevibacterium pusillum ATCC 19096 | 4.1 |
| Protaminobacter alboflavus ATCC 8458 | 3.4 |
| Proteus rettegeri AJ 2770 (FERM BP-941) | 2.8 |
| Haemophilus influenzae ATCC 9134 | 2.6 |
| Micrococcus luteus ATCC 4698 | 5.7 |
| Mycoplana dimorpha ATCC 4279 | 7.3 |
| Microbacterium lacticum ATCC 8180 | 3.8 |
| Rhizobium melilotti AJ 2823 (FERM BP-6565) | 2.9 |
| Rhodococcus rhodochraus ATCC 19149 | 7.2 |

Example 3

Into a Sakaguchi flask (500 ml) was placed 50 ml of a nutrient medium (pH 7.0) containing 5 g/l yeast extract, 10 g/l meat extract, 10 g/l peptone and 5 g/l NaCl and sterilized at 120° C. for 20 minutes. Each one platinum loop of Klebsiella pneumoniae IFO 3321, cultured on the bouillon agar slant at 30° C. for 16 hours was inoculated to this and cultured with shaking at 30° C. for 18 hours. Cells were separated from the obtained culture by centrifugation, then washed with 50 mM phosphate buffer (pH 7.0) and centrifuged again to prepare washed cells.

The washed cells described above were added to 10 ml of 50 mM phosphate buffer (pH 7.0) containing 100 mM thymidine and 100 mM 2,6-diaminopurine hemisulfate to a washed cell concentration of 50 g/l and reacted at 60° C. for 2 hours.

The concentration of 2,6-diaminopurine-2'-deoxyriboside produced in the reaction solution was measured by high performance liquid chromatography. The result showed that 15.2 g/l of 2,6-diaminopurine-2'-deoxyriboside was produced.

Example 4

To 5 ml of 50 mM phosphate buffer solution containing 20.0 g/l 2,6-diaminopurine-2'-deoxyriboside and 5 ml (pH 7.0) of the reacted solution obtained in Example 2 using Klebsiella pneumoniae IFO 3321 (containing 16.9 g/l 2,6-diaminopurine-2'-deoxyriboside) was added each 50 µl of adenosine deaminase (50% glycerol solution, derived from calf intestine, about 200 U/mg) manufactured by Boehringer. The mixtures were allowed to react at 25° C. for 1 hour while adjusting pH to 7.0.

The concentration of 2'-deoxyguanosine produced in the reaction solution was measured by high performance liquid chromatography. The results showed that the concentration was 19.8 g/l (conversion molar yield: 99%) and 16.8 g/l (conversion molar yield: 99%), respectively.

Example 5

Into a Sakaguchi flask (500 ml) was placed 50 ml of a nutrient medium (pH 7.0) containing 5 g/l yeast extract, 10 g/l meat extract, 10 g/l peptone and 5 g/l NaCl and sterilized at 120° C. for 20 minutes. One platinum loop of Arthrobacter ureafaciens (FERM BP-2472), cultured on the bouillon agar slant at 30° C. for 16 hours was inoculated to this and cultured with shaking at 30° C. for 16 hours. Cells were separated from the obtained culture by centrifugation, then washed with 50 mM Tris-HCl buffer (pH 7.2) and centrifuged again to prepare washed cells.

The washed cells described above were added to 50 mM Tris-HCl buffer (pH 7.2) containing 20.0 g/l 2,6-diaminopurine-2'-deoxyriboside to a concentration of 5 g/l and reacted at 30° C. for 3 hours while keeping pH at 7.2. The concentration of 2'-deoxyguanosine produced in the reaction solution was measured by high performance liquid chromatography. The result showed that the concentration was 19.8 g/l (conversion molar yield: 99%), respectively.

As described above, the present invention enables production of 2,6-diaminopurine-2'-deoxyriboside and 2'-deoxyguanosine in a high yield, with ease and at low costs.

Obviously, numerous modifications and variations of the present invention are possible in light of the above teachings. It is therefore to be understood that within the scope of the appended claims, the invention may be practiced otherwise than as specifically described herein.

Japanese priority application 9-313,207, filed on Nov. 14, 1997, is incorporated herein by reference in its entirety.

What is claimed is:

1. A process for preparing 2'-deoxyguanosine, comprising:

contacting 2'-deoxyribose-1-phosphoric acid or a salt thereof and 2,6-diaminopurine with a microorganism which produces, 2,6-diaminopurine-2'-deoxyriboside from 2'-deoxyribose-1-phosphoric acid or a salt thereof and 2,6-diaminopurine, or with cells or cell lysate of said microorganism; and contacting the 2,6-diaminopurine-2'-deoxyriboside with an adenosine deaminase in an aqueous medium to produce the 2'-deoxyguanosine;

wherein said microorganism belongs to a genus selected from the group consisting of Achromobacter, Agrobacterium, Acinetobacter, Alcaligenes, Arthrobacter, Aeromonas, Escherichia, Enterobacter, Erwinia, Xanthomonas, Klebsiella, Kurthia, Kluyvera, Corynebacterium, Sartina, Salmonella, Citrobacter, Pseudomonas, Streptomyces, Sporosarcina, Staphyrococcus, Serratia, Cellulomonas, Nocardia, Hafnia, Vibrio, Flavobacterium, Planococcus, Brevibacterium, Protaminobacter, Proteus, Haemophilus, Micrococcus, Mycoplana, Microbacterium, Rhizobium and Rhodococcus.

2. The process of claim 1, wherein the 2,6-diaminopurine-2'-deoxyriboside and the adenosine deaminase are contacted at 5 to 50° C. at a pH of 4 to 10.

3. The process of claim 1, wherein the 2,6-diaminopurine-2'-deoxyriboside and the adenosine deaminase are contacted for 10 minutes to 5 days.

4. A process for synthesizing an oligonucleotide, comprising: preparing 2'-deoxyguanosine by the process according to claim 1, and then incorporating said 2,6-diaminopurine-2'-deoxyriboside into an oligonucleotide.

5. The process of claim 1, wherein said cells or cell lysate is acetone-dried cells of said microorganism, triturated cells of said microorganism, cells of said microorganism treated with an ultrasonic oscillator or a Dynomill or French press, cells of said microorganism contacted with a surfactant or toluene, cells of said microorganism treated with lysozyme or a protease, a protein fraction obtained by treating a cell extract of said microorganism dialysis, or immobilized cells of said microorganism.

* * * * *

UNITED STATES PATENT AND TRADEMARK OFFICE
CERTIFICATE OF CORRECTION

PATENT NO. : 6,197,552 B1
DATED : March 6, 2001
INVENTOR(S) : Kenzo Yokozeki, et al.

It is certified that error appears in the above-identified patent and that said Letters Patent is hereby corrected as shown below:

Title page, Item (22),
The filing date is listed incorrectly. Item (22) should read as follows:

-- (22) Filed: Nov. 16, 1998 --

Signed and Sealed this

Twenty-fifth Day of September, 2001

*Attest:*

*Attesting Officer*

NICHOLAS P. GODICI
*Acting Director of the United States Patent and Trademark Office*